United States Patent [19]

Daftary et al.

[11] Patent Number: 5,470,230
[45] Date of Patent: Nov. 28, 1995

[54] ANATOMICAL DENTAL IMPLANT WITH EXPANDABLE ROOT

[76] Inventors: Fereidoun Daftary, 50 N. La Gienega Blvd., No. 206, Beverly Hills, Calif. 90210; Oded Bahat, 414 N. Camden Dr., Beverly Hills, Calif. 90210

[21] Appl. No.: 315,603

[22] Filed: Sep. 30, 1994

[51] Int. Cl.$^6$ .................................................. A61C 8/00
[52] U.S. Cl. ............................................. 433/174; 433/173
[58] Field of Search .................................... 433/173, 174, 433/175, 176

[56] References Cited

U.S. PATENT DOCUMENTS

| | | | |
|---|---|---|---|
| 2,721,387 | 10/1955 | Ashuckian | 433/173 |
| 3,579,831 | 5/1971 | Stevens et al. | |
| 3,708,883 | 1/1973 | Flander | |
| 4,011,602 | 3/1977 | Rybicki et al. | |
| 4,220,712 | 9/1980 | Staffolani | 433/173 |
| 4,468,201 | 8/1994 | Fukuyo | 433/176 |
| 4,588,381 | 5/1986 | Caracciolo | 433/173 |
| 5,004,421 | 4/1991 | Lazarof | 433/173 |
| 5,219,287 | 6/1993 | Nishihara | 433/201.1 |

FOREIGN PATENT DOCUMENTS

| | | | |
|---|---|---|---|
| 3326710 | 1/1985 | Germany | 433/174 |
| 0728855 | 5/1980 | U.S.S.R. | 433/176 |

*Primary Examiner*—Cary E. O'Connor
*Attorney, Agent, or Firm*—Thomas I. Rozsa; Tony D. Chen

[57] ABSTRACT

A dental implant assembly for supporting a dental component on a patient's jawbone. The dental implant assembly is fitted into a hole drilled in the jawbone. The dental implant assembly comprises an implant member having a hollow bottom sleeve split into multiple segments, a fixed shaft located inside the split bottom sleeve, and an expander member movably mounted on the fixed shaft and having a ramped surface engaging with the at least two split segments. The expander member is engaged with the bottom of the jawbone hole, and caused to move on the shaft as the implant member is installed into the jawbone hole, to thereby force the split segments to expand outwardly against and tightly engage with the interior sidewall of the jawbone hole. Therefore, the dental implant assembly can be securely installed into the patient's jawbone in a single step without any additional and separate step to operate the expander.

20 Claims, 3 Drawing Sheets

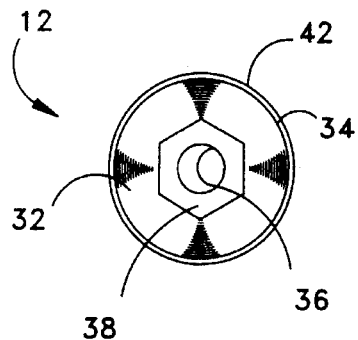
FIG.4
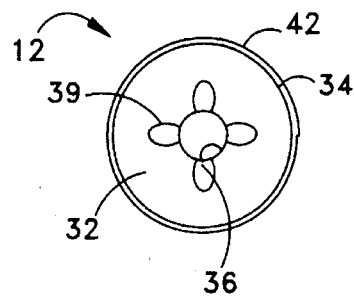
FIG.5
FIG.7
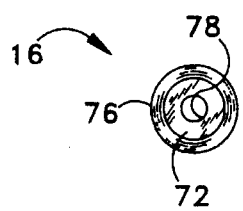
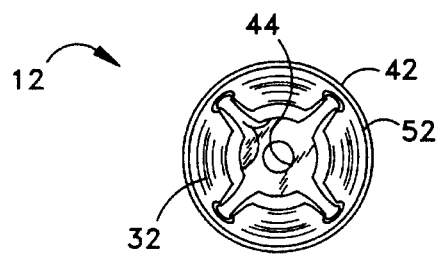
FIG.6
FIG.8
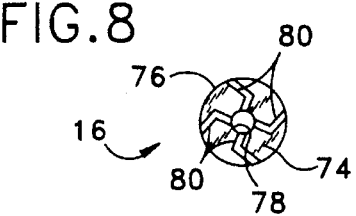
FIG.10
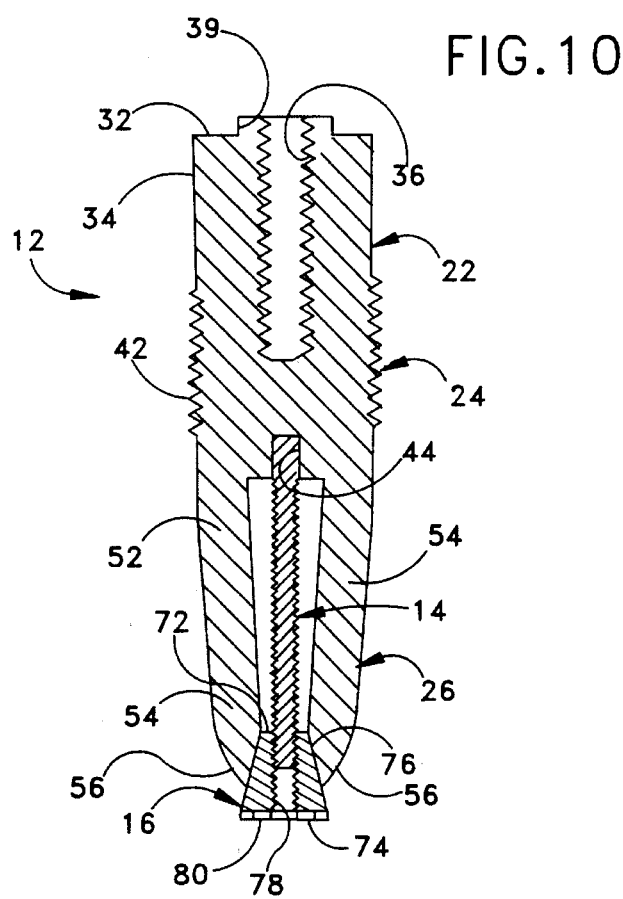
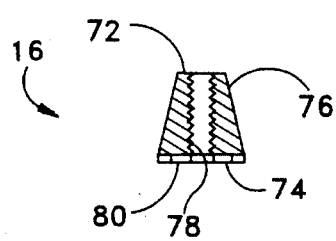
FIG.9

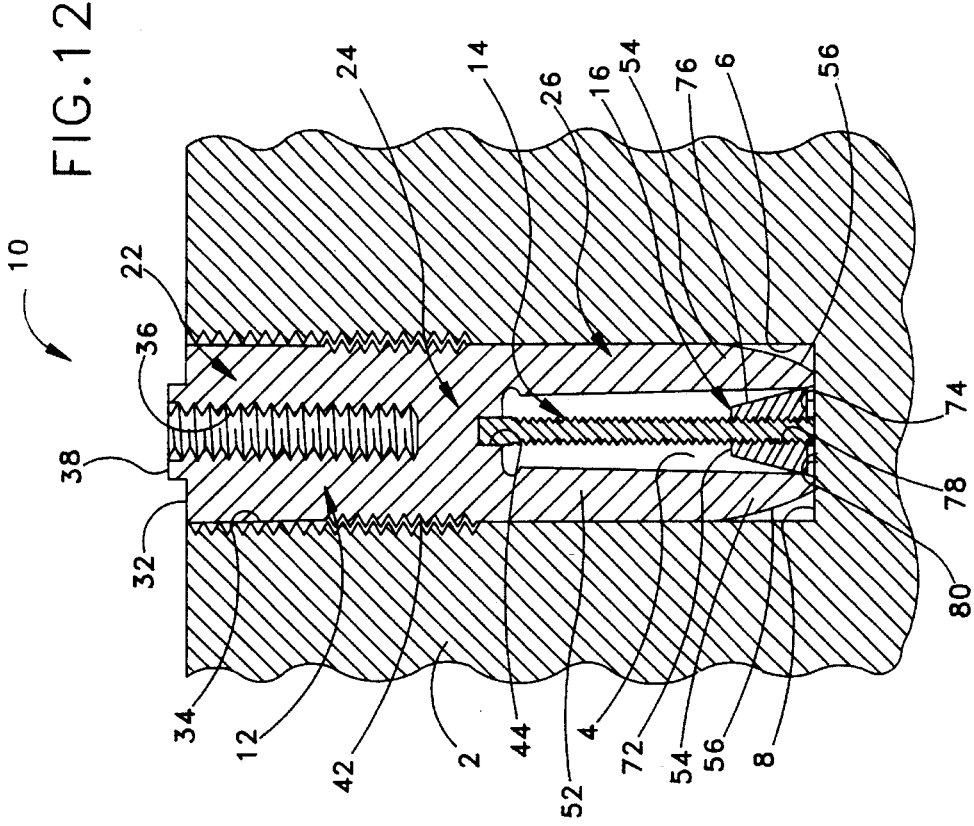
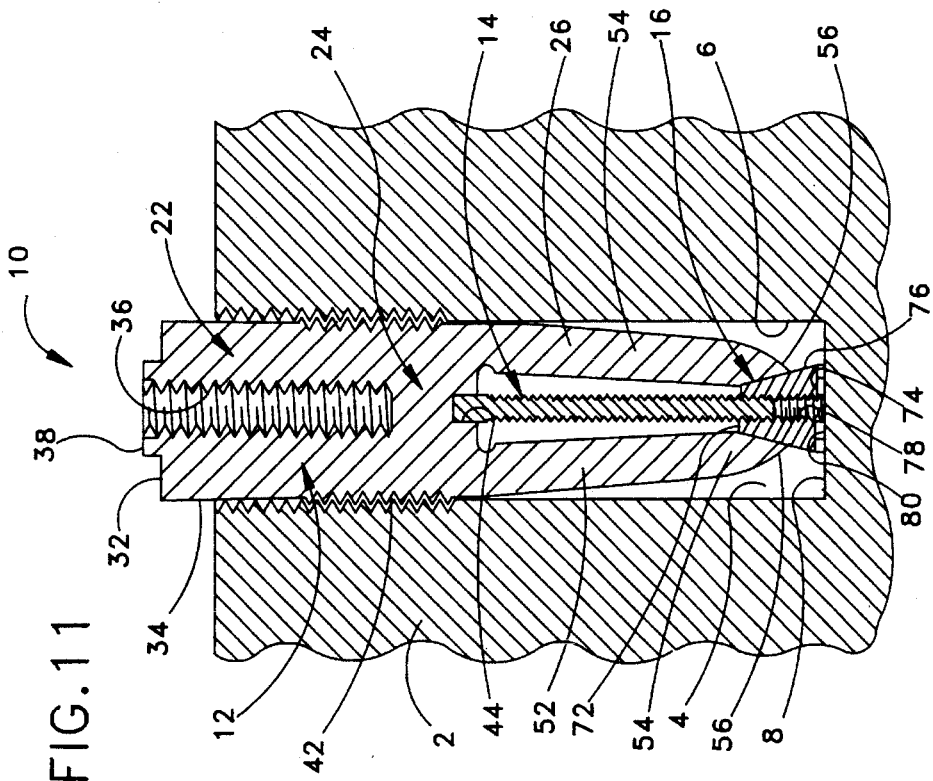

ANATOMICAL DENTAL IMPLANT WITH EXPANDABLE ROOT

BACKGROUND OF THE INVENTION

1. Field of The Invention

The present invention relates to the field of anatomical restoration dental implant systems. More particularly the present invention relates to the field of the design and construction of dental implants.

2. Description of The Prior Art

Dental implants are widely used in anatomical restoration dental operations or surgeries. They are used primarily for attaching various dental components to the jawbone of a patient. One of the inventors of the present invention is also the inventor and patentee of many patented dental restoration systems and dental components as disclosed in U.S. Pat. Nos. 5,035,619, 5,073,111, 5,145,372, 5,213,502 and 5,297,963. This invention is part of a constant desire and effort by the inventors to improve and advance dental restoration systems.

A typical conventional dental implant has a generally cylindrical shaped body which is to be imbedded in a patient's jawbone by first drilling a hole in the patient's jawbone and then inserting the implant into the hole. The implant is usually threadedly fitted or press-fitted in the hole.

Most conventional implants have a fixed bottom which has a definite dimension. Oftentimes when a hole in a patient's jawbone is improperly drilled, e.g., the hole is drilled too big, there will be a size discrepancy between the hole and the implant. This will result in loose implant in the jawbone and possible increased rate of implant loss.

One way to solve the problem of mismatch is to utilize an implant which has a split bottom with an expanding mechanism, so that once the implant is inserted into an oversized hole, the bottom of the implant can split and expand to better fit within the hole.

The following eight (8) patents are the closest prior art references which relate to dental implants with a split bottom:

1. U.S. Pat. No. 5,219,287 issued to Nishihara on Jun. 5, 1993 for "Artificial Dental Root Having Function of Natural Dental Root" (hereafter the "Nishihara Patent").

2. U.S. Pat. No. 5,004,421 issued to Lazarof on Apr. 2, 1991 for "Dental Implant and Method of Using the Same" (hereafter the "Lazarof Patent").

3. U.S. Pat. No. 4,588,381 issued to Caracciolo on May 13, 1986 for "Universal Pin for Oral Implantoprosthesis" (hereafter the "Caracciolo Patent").

4. U.S. Pat. No. 4,468,201 issued to Fukuyo on Aug. 28, 1994 for "Dental Endosseous Implant" (hereafter the "Fukuyo Patent").

5. U.S. Pat. No. 4,220,712 issued to Staffolani on Sep. 2, 1980 for "Dental Implant and Method of Inserting" (hereafter the "Staffolani Patent").

6. U.S. Pat. No. 4,011,602 issued to Rybicki et al. on Mar. 15, 1977 for "Porous Expandable Device for Attachment to Bone Tissue" (hereafter the "Rybicki Patent").

7. U.S. Pat. No. 3,708,883 issued to Flander on Jan. 9, 1973 for "Dental Implant and Method for Using the Same" (hereafter the "Flander Patent").

8. U.S. Pat. No. 3,579,831 issued to Stevens et al. on May 25, 1971 for "Bone Implant" (hereafter the "Stevens Patent").

The Lazarof Patent discloses a dental implant. The dental implant can be positively secured within a bore in a jawbone by an expander mechanism. The implant has an upper threaded portion and a lower skirt portion. The skirt portion is split into four separately expandable bone anchor segments. The expander mechanism includes an expander means which has an upper threaded portion and a lower frusto-conical portion. The expander means can be rotated by a removable Allen wrench by extending the Allen wrench through the internal bore of the implant. When the expander is rotated, its upper threaded portion is engaged with the internal threads of the implant which causes the expander means to move upwardly, which in turn causes its lower frusto-conical portion to engage with the four separately expandable bone anchor segments of the implant and causes them to expand outwardly.

The Caracciolo Patent discloses a "universal" pin for oral implantoprosthesis. The bottom part of the "universal" pin is split. In a first embodiment, the pin is hollow and a solid element is inserted from the top of the pin all the way towards the bottom, which causes the split bottom of the pin to expand outwardly. In a second embodiment, a wedge base is inserted from the bottom of the pin, which also causes the split bottom of the pin to expand outwardly. When the bottom part expands outwardly, the "universal" pin has a double taper configuration.

The Staffolani Patent discloses a dental implant with various shaped lower tips. The tips can be forced by the insertion of a pin to rotate out and upwardly into the bone.

The Rybicki Patent discloses an expandable cylinder for attachment to bone tissue. The expandable cylinder has splits which allows the cylinder to expand outwardly when a tapered pin is drawn into the cylinder by tightening a threaded nut.

The Flander Patent discloses a dental implant having a split bottom. An elongated shaft is extended through the implant. A small nut is threaded on the upper end of the shaft for "pulling" the shaft upwardly. The lower part of the shaft has a spreader end portion which acts as a wedge to cause the implant to expand when the shaft is pulled upwardly.

The remaining prior art patents are not as close and are discussed here briefly for reference.

The Nishihara Patent discloses an artificial dental root made of a shape-memorizing alloy capable of changing the apex morphology of the artificial root after implantation so as to stay in the jawbone. The Fukuyo Patent discloses a dental endosseous implant utilizing various deflectable legs which have shape-memory effects for securing the implant. The Stevens Patent discloses a bone implant having an axially extending notch at its bottom to provide a pair of springy threaded portions capable of resiliently flexing toward and away from each other so as to enhance the self-threading action of the implant.

From the above review it can be seen that the overall idea of utilizing an implant with split bottom to securely attach the implant to the jawbone has been disclosed. Various mechanisms have been disclosed by the prior art to achieve the purpose of causing the split bottom of the implant to expand. For example, in the Staffolani Patent and the first embodiment of the Caracciolo Patent, a solid shaft is inserted from the top of the implant to force the split bottom of the implant to expand outwardly, whereas in the Flander Patent and the Rybicki Patent, a solid shaft is drawn upwardly through the implant so that its wedge shaped bottom can cause the split bottom of the implant to expand outwardly.

Two prior patents have particularly disclosed the idea of using a separate small wedge to engage and expand the split bottom of the implant. The first is the Caracciolo Patent where a small wedge shaped base element is utilized in the second embodiment. This is a very modest and preliminary design and does not adequately satisfy the need for precise control in dental operations. The second, however, is the Lazarof Patent where an expander means is utilized which can be drawn upwardly by threading it on the internal surface of the implant and thereby causes the split bottom of the implant to expand outwardly. This is a much more detailed and sophisticated design.

However, there is a major drawback in the prior art dental implant with expandable bottom. For example, in the Lazarof Patent, the implant is first threaded into the jawbone, then the expander means is tightened by using an Allen wrench. This involves two separate manipulating steps to secure the implant to the patient's jawbone.

It is desirable to have a new design and construction of a dental implant with a split bottom which can be secured to the jawbone of a patient in one single step. It is desirable to design and construct an expanding mechanism which causes the expander to be automatically tightened when the implant is threaded into the jawbone.

SUMMARY OF THE INVENTION

The present invention is a dental implant assembly. The dental implant assembly is typically used for supporting a dental component on a patient's jawbone, where the dental implant is fitted into a hole drilled in the patient's jawbone.

In a preferred embodiment of the present invention, the dental implant assembly includes three pieces: an integral body member, an internal shaft member, and an expander member. The shaft member is fixed to the body member. As an alternative embodiment, the shaft member may be an integral part of the body member.

Described generally, the integral body member has an upper portion and a lower portion. The upper portion has an exterior surface for engaging with the interior sidewall of the jawbone hole, and an upward facing interior bore for adopting the dental component. The lower portion has a hollow sleeve split into a multiplicity of segments.

The internal shaft member has a top end and a threaded lower portion. The top end is non-rotatably attached to the body member and located inside its split lower portion. In the preferred embodiment, the shaft member is press-fittedly attached to the body member. However, in one alternative engagement, the shaft member is integrally attached to, or simply an integral part of, the body member.

The expander member has a small top end, a large bottom end, a ramped exterior surface, and a threaded interior bore extending from the top end to the bottom end for threadedly engaging with the threaded lower portion of the internal shaft member. The exterior surface of the expander member engages with the multiplicity of segments of the lower portion of the integral body member. The bottom end of the expander member has a plurality of curved blades for anti-rotation engagement with the bottom of the jawbone hole.

The integral body member can be rotated by a driving tool when it is installed into the jawbone hole. The fixedly attached internal shaft member is also rotated when the integral body member is rotated, which in turn causes the expander member to move upwardly on the internal shaft member, because expander member is prevented from rotating by its anti-rotation engagement with the bottom of the jawbone hole. As the expander member moves upwardly on the internal shaft, it forces the multiplicity of segments of the lower portion of the integral body member to expand outwardly against the interior sidewall of the jawbone hole, thereby tightly securing the implant assembly into the patient's jawbone.

The primary advantage of the present invention is that it only requires a one-step process to securely install the dental implant assembly into a patient's jawbone. The dental implant assembly can be securely installed into the patient's jawbone in a single step without any additional and separate step to operate the expander. When the body member is threaded into the jawbone hole, the expander member is automatically tightened because it has an anti-rotation mechanism which prevents it from rotation.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 4 is a top view of a preferred embodiment of the integral body member.

FIG. 5 is a top view of an alternative embodiment of the integral body member.

FIG. 6 is a bottom view of the preferred embodiment of the integral body member.

FIG. 7 is a top view of a preferred embodiment of the expander member.

FIG. 8 is a bottom view of the preferred embodiment of the expander member.

FIG. 9 is a side view of the preferred embodiment of the expander member.

FIG. 10 is a cross-sectional view of the present invention dental implant assembly, taken along line 10—10 of FIG. 1.

FIG. 11 is an illustrative cross-sectional view of the present invention dental implant assembly partially installed in a hole drilled in a patient jawbone.

FIG. 12 is an illustrative cross-sectional view of the present invention dental implant assembly completely installed in the hole drilled in the patient jawbone.

DESCRIPTION OF THE PREFERRED EMBODIMENT

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
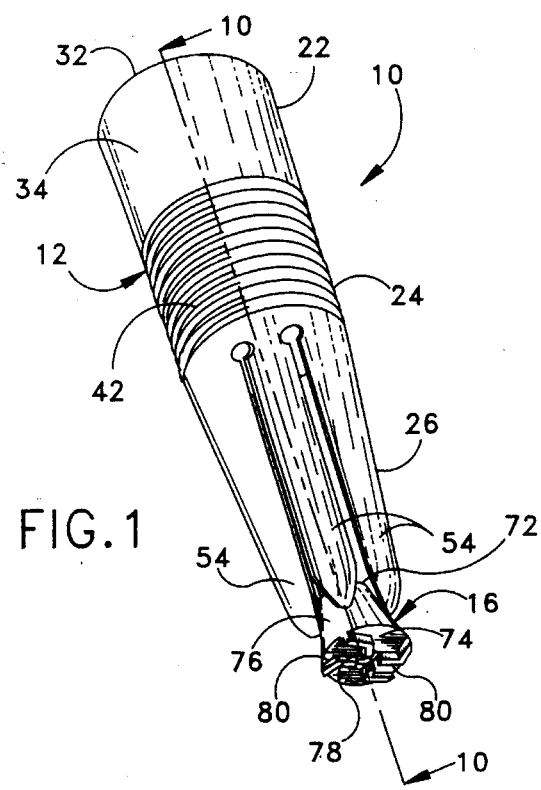
FIG. 1 is a perspective view of the present invention dental implant assembly.
Figure 2:
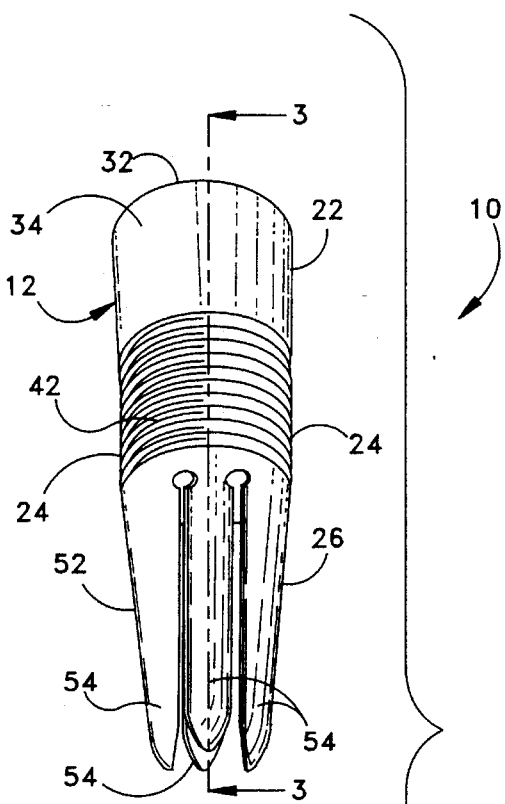
FIG. 2 is an exploded view of the present invention dental implant assembly, showing the integral body member, the internal shaft member and the expander member.
Figure 3:
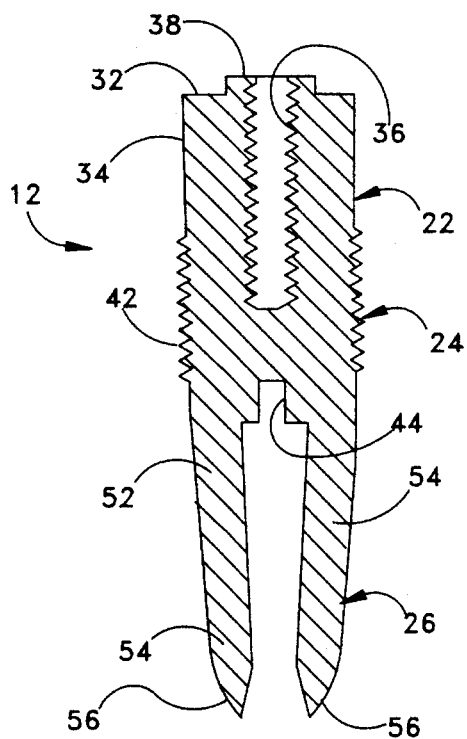
FIG. 3 is a cross-sectional view of the integral body member, taken along line 3—3 of FIG. 2.

Referring to FIGS. 1 and 2, there is shown at 10 the present invention dental implant assembly for supporting a dental component (not shown) on a patient's jawbone. The dental implant assembly 10 is to be fitted into a hole drilled in a patient's jawbone. In a preferred embodiment, the dental implant assembly includes an implant body member 12, an internal shaft member 14, and an expander member 16. In an alternative embodiment, the internal shaft member 14 may be an integral part of the implant body member 12.

Referring to FIGS. 1 through 6, in the preferred embodiment of the present invention, the implant body member 12 is a generally cylindrical shaped integral piece. The integral body member 12 has a top section 22, a middle section 24 and a bottom section 26. The top section 22 of the integral body member 12 has a top end 32, an abrasive exterior surface 34, and an upward facing interior threaded bore 36. The middle section 24 of the integral body member 12 has a threaded exterior surface 42, and a downward facing interior bore 44. The bottom section 26 of the integral body member 12 has a hollow sleeve 52 which is split into a plurality of longitudinally elongated segments 54. Each split segment 54 has a bottom end 56.

In the preferred embodiment, the hollow sleeve 52 of the bottom section 26 of the integral body member 12 is split into four (4) symmetrical segments. However, the number of split segments may vary, and they do not have to be symmetric. The minimum number of split segments is two (2).

In addition, in another alternative embodiment of the integral body member 12, the top section 22 may have exterior screw threads or a smooth exterior surface, and the middle section 24 may have an abrasive exterior surface or a smooth exterior surface. When the exterior surfaces of the top section 22 and middle section 24 become identical, these two sections blend into one upper portion of the integral body member 12, leaving the bottom section 26 as the lower portion of the integral body member 12.

As shown in FIG. 4, at the top end of the integral body member 12, there is a hexagonal lip for anti-rotation engagement with the attached dental component (not shown). The hexagonal lip also serves as means for receiving a driving tool such as a small wrench (not shown), which is used to rotate the integral body member. Of course the hexagonal lip shown in FIG. 4 may be substituted by a hexagonal socket or other types of lip or socket to suit different needs for the attachment of various dental components.

Moreover, in other alternative embodiments of the integral body member 12, other types of arrangements may also be made to accommodate different tools. For example, as shown in FIG. 5, there are four (4) dents 39 which are provided at the top end 32 of the integral body member 12 for receiving a cross-tip screw driver (not shown).

Referring back to FIG. 2, the elongated internal shaft member 14 has a top end 62 and a bottom end 64. The shaft member 14 also has screw threads 66 along a substantial portion of its length except the top end 62. In fact, the length of the threaded portion may vary, as long as the bottom portion of the shaft member 14 has screw threads. In the preferred embodiment there are no screw threads at the top end 62 of the shaft member 14 so that it can be press-fitted into the downwardly facing interior bore 44 of the middle section 24 of the integral body member 12.

Referring to FIGS. 7 through 9, the expander member 16 has a frusto-conical shaped configuration. It has a small top end 72, a large bottom end 74, a ramped or beveled exterior surface 76, and a threaded interior bore 78 extending from the top end 72 to the bottom end 74. At the bottom end 74 there are further provided a plurality of downwardly protruding thin blades 80. Each blade 80 is curved to increase its functional or effective length.

Referring to FIG. 10, the top end 62 of the internal shaft member 14 is press-fitted into the downward facing interior bore 44 of the middle section 24 of the integral body member 12. This is to ensure a non-rotatable attachment of the internal shaft member 14. Once attached to the integral body member 12, the shaft member 14 is located inside the split bottom section 26 of the integral body member 12.

The expander member 16 is threaded onto the shaft member 14. The screw threads on the shaft member 14 and expander member 16 are arranged in a manner such that when the bottom end 64 of the shaft member 14 is threadedly rotated into the interior bore 78 of the expander member 16, the expander member 16 will move upwardly on and along the shaft member 14. As the expander member 16 is threaded on the bottom end 64 of the shaft member 14, the ramped or beveled exterior surface 76 of the expander member 16 is engaging with the respective bottom ends 56 of the plurality of longitudinally elongated segments 54 of the bottom section 26 of the integral body member 12. When the expander member 16 moves further upwardly on the shaft member 14, it will force the split segments 54 to expand outwardly.

Now turning to FIGS. 11 and 12. FIG. 11 shows that the dental implant assembly 10 is partially installed into a hole 4 drilled in a jawbone 2 of a patient. The jawbone hole 4 has an interior sidewall 6 and a bottom 8. The abrasive exterior surface 34 of the top section 22 of the integral body member 12 is frictionally engaged with the interior sidewall 6 of the jawbone hole 4, and the exterior threads 42 of the middle section 24 of the integral body member 12 are threaded into the interior sidewall 6 of the jawbone hole 4.

As the dental implant assembly 10 is threaded or otherwise inserted into the hole 4, the bottom blades 80 of the expander member 16 will first come into contact with the bottom 8 of the jawbone hole 4. When the bottom blades 80 bite into the bottom 8 of the jawbone hole 4, they act as an anti-rotation mechanism which prevents the expander member 16 from rotating.

As the integral body member 12 is further threaded into the jawbone hole 4, the internal shaft member 14 will rotate with the integral body member 12. This causes the expander member 16 to move upwardly on the internal shaft member 14, to thereby force the split segments 54 of the bottom section 26 of the integral body member 12 to expand outwardly against, and tightly engage with, the interior sidewall 6 of the jawbone hole 4.

It is noted that the preferred press-fit attachment between the shaft member 14 and the integral body member 12 ensures that the there is no relative rotation therebetween, but rather the shaft member 14 rotates together with the integral body member 12 as the latter is rotated by a driving tool. However, press-fitting is only one of the many methods which can be utilized for fixedly attaching the shaft member 14 to the implant body member 12. For example, the shaft member 14 can have screw threads over its entire length, including its top end 62, such that the shaft member can be threadedly attached to the body member 12, as long as it is threaded in an opposite direction to the direction by which the body member 12 is threaded into the jawbone hole 4, so that as the body member 12 is threaded into the jawbone hole 4, the body member 12 forces the shaft member 14 to rotate with it. In addition, as an alternative embodiment, the shaft member 14 may be an integral or unitary part of the implant body member 12.

FIG. 12 shows that the dental implant assembly 10 is completely installed into the jawbone hole 10 in the patient's jawbone 2. The expanding mechanism of the present invention dental implant assembly 10 ensures that even if the jawbone hole 4 is drilled with error such that it is oversized, the dental implant assembly 10 can still be tightly installed therein. The upward facing interior bore 36 in the integral body member 12 is now ready for adopting a dental component (not shown).

One of the advantages of the present invention dental implant assembly is that it can be securely installed into the patient's jawbone in a single step without any additional and separate step to operate the expander. This is because the expander 16 is self-locked to the bottom 8 of the jawbone hole 4 and automatically moves upwardly on the internal shaft member 14 as the implant body member 12 is threaded into the jawbone hole 4. Of course, this simple step is just one of the many ways to utilize the present invention.

Defined in detail, the present invention is a dental implant assembly for supporting a dental component on a patient's jawbone, the dental implant assembly to be fitted into a hole which is drilled in the jawbone and has an interior sidewall and a bottom, the dental implant assembly comprising: (a) a generally cylindrical integral body member having a top section, a middle section and a bottom section; (b) the top section of the integral body member having a top end, an abrasive exterior surface for frictionally engaging with the interior sidewall of the jawbone hole, and an upward facing interior threaded bore for adopting the dental component; (c) the middle section of the integral body member having a threaded exterior surface for threadedly fastening to the interior sidewall of the jawbone hole, and a downward facing interior bore; (d) the bottom section of the integral body member having a hollow sleeve split into a multiplicity of longitudinally elongated segments each having a bottom end; (e) an elongated internal shaft member having a top end and a bottom end, and screw threads along a substantial portion of its length except the top end; (f) the top end of the internal shaft member press-fitted into the downward facing interior bore of the middle section of the integral body member for non-rotatably attaching the internal shaft member inside the split bottom section of the integral body member; (g) a frusto-conical shaped expander member having a small top end, a large bottom end, a beveled exterior surface, and a threaded interior bore extending from the top end to the bottom end for threadedly engaging with the bottom end of the internal shaft member; (h) the beveled surface of the expander member engaging with the bottom ends of the multiplicity of longitudinally elongated segments of the bottom section of the integral body member; (i) the bottom end of the expander member having means for anti-rotation engagement with the bottom of the jawbone hole; and (j) the top end of the top section of the integral body member having means adaptable to a driving tool for rotating the integral body member to install it into the jawbone hole, causing the internal shaft member also to rotate, which in turn causes the expander member to move upwardly on the internal shaft member, to thereby force the multiplicity of longitudinally elongated segments of the bottom section of the integral body member to expand outwardly against and tightly engage with the interior sidewall of the jawbone hole; (k) whereby the dental implant assembly can be securely installed into the patient's jawbone in a single step without any additional and separate step to operate the expander.

Defined broadly, the present invention is a dental implant assembly for supporting a dental component on a patient's jawbone, the dental implant assembly to be fitted into a hole which is drilled in the jawbone and has an interior sidewall and a bottom, the dental implant assembly comprising: (a) an integral body member having an upper portion and a lower portion; (b) the upper portion of the integral body member having an exterior surface for engaging with the interior sidewall of the jawbone hole, and an upward facing interior bore for adopting the dental component; (c) the lower portion of the integral body member having a hollow sleeve split into a multiplicity of segments; (d) an internal shaft member having a top end and a threaded lower portion, the top end non-rotatably attached to the integral body member and located inside the split lower portion thereof; (e) an expander member having a small top end, a large bottom end, an exterior surface, and a threaded interior bore for threadedly engaging with the threaded lower portion of the internal shaft member; (f) the exterior surface of the expander member engaging with the multiplicity of segments of the lower portion of the integral body member; (g) the bottom end of the expander member having means for anti-rotation engagement with the bottom of the jawbone hole; and (h) the integral body member further having means adaptable to a driving tool for rotating the integral body member to install it into the jawbone hole, causing the internal shaft member also to rotate, which in turn causes the expander member to move upwardly on the internal shaft member, to thereby force the multiplicity of segments of the lower portion of the integral body member to expand outwardly against and tightly engage with the interior sidewall of the jawbone hole; (i) whereby the dental implant assembly can be securely installed into the patient's jawbone in a single step without any additional and separate step to operate the expander.

Defined more broadly, the present invention is a dental implant assembly for supporting a dental component on a patient's jawbone, the dental implant assembly to be fitted into a hole which is drilled in the jawbone and has an interior sidewall and a bottom, the dental implant assembly comprising: (a) an implant member having a hollow bottom sleeve split into at least two segments, and a fixed shaft located inside the split bottom sleeve; (b) an expander member movably mounted on the fixed shaft and having a ramped surface engaging with the at least two split segments; and (c) the expander member engaged with the bottom of the jawbone hole, and caused to move on the shaft as the implant member is installed into the jawbone hole, to thereby force the at least two split segments of the bottom sleeve of the implant member to expand outwardly against and tightly engage with the interior sidewall of the jawbone hole; (d) whereby the dental implant assembly can be securely installed into the patient's jawbone in a single step without any additional and separate step to operate the expander.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modification in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. A dental implant assembly for supporting a dental component on a patient's jawbone, the dental implant assembly to be fitted into a hole which is drilled in the jawbone and has an interior sidewall and a bottom, the dental implant assembly comprising:
   a. a generally cylindrical integral body member having a top section, a middle section and a bottom section;
   b. said top section of said integral body member having a top end, an abrasive exterior surface for frictionally engaging with said interior sidewall of said jawbone hole, and an upward facing interior threaded bore for adopting said dental component;
   c. said middle section of said integral body member having a threaded exterior surface for threadedly fastening to said interior sidewall of said jawbone hole, and a downward facing interior bore;
   d. said bottom section of said integral body member having a hollow sleeve split into a multiplicity of longitudinally elongated segments each having a bottom end;
   e. an elongated internal shaft member having a top end and a bottom end, and screw threads along a substantial portion of its length except the top end;
   f. said top end of said internal shaft member press-fitted into said downward facing interior bore of said middle section of said integral body member for non-rotatably attaching said internal shaft member inside said split bottom section of said integral body member;
   g. a frusto-conical shaped expander member having a small top end, a large bottom end, a beveled exterior surface, and a threaded interior bore extending from the top end to the bottom end for threadedly engaging with said bottom end of said internal shaft member;
   h. said beveled surface of said expander member engaging with said bottom ends of said multiplicity of longitudinally elongated segments of said bottom section of said integral body member;
   i. said bottom end of said expander member having means for anti-rotation engagement with said bottom of said jawbone hole; and
   j. said top end of said top section of said integral body member having means adaptable to a driving tool for rotating said integral body member to install it into said jawbone hole, causing said internal shaft member also to rotate, which in turn causes said expander member to move upwardly on said internal shaft member, to thereby force said multiplicity of longitudinally elongated segments of said bottom section of said integral body member to expand outwardly against and tightly engage with said interior sidewall of said jawbone hole;
   k. whereby said dental implant assembly can be securely installed into said patient's jawbone in a single step without any additional and separate step to operate said expander.

2. The dental implant assembly as defined in claim 1 wherein said multiplicity of split segments are symmetrical segments.

3. The dental implant assembly as defined in claim 1 wherein said anti-rotation engagement means includes a multiplicity of downward protruding curved thin blades.

4. The dental implant assembly as defined in claim 1 wherein said means adaptable to a driving tool includes an upwardly extending polygonal lip.

5. The dental implant assembly as defined in claim 1 wherein said means adaptable to a driving tool includes a multiplicity of small dents.

6. A dental implant assembly for supporting a dental component on a patient's jawbone, the dental implant assembly to be fitted into a hole which is drilled in the jawbone and has an interior sidewall and a bottom, the dental implant assembly comprising:
   a. an integral body member having an upper portion and a lower portion;
   b. said upper portion of said integral body member having an exterior surface for engaging with said interior sidewall of said jawbone hole, and an upward facing interior bore for adopting said dental component;
   c. said lower portion of said integral body member having a hollow sleeve split into a multiplicity of segments;
   d. an internal shaft member having a top end and a threaded lower portion, the top end non-rotatably attached to said integral body member and located inside said split lower portion thereof;
   e. an expander member having a small top end, a large bottom end, an exterior surface, and a threaded interior bore for threadedly engaging with said threaded lower portion of said internal shaft member;
   f. said exterior surface of said expander member engaging with said multiplicity of segments of said lower portion of said integral body member;
   g. said bottom end of said expander member having means for anti-rotation engagement with said bottom of said jawbone hole; and
   h. said integral body member further having means adaptable to a driving tool for rotating said integral body member to install it into said jawbone hole, causing said internal shaft member also to rotate, which in turn causes said expander member to move upwardly on said internal shaft member, to thereby force said multiplicity of segments of said lower portion of said integral body member to expand outwardly against and tightly engage with said interior sidewall of said jawbone hole;
   i. whereby said dental implant assembly can be securely installed into said patient's jawbone in a single step without any additional and separate step to operate said expander.

7. The dental implant assembly as defined in claim 6 wherein said exterior surface of said upper portion of said integral body member has a section which is a threaded surface.

8. The dental implant assembly as defined in claim 6 wherein said exterior surface of said upper portion of said integral body member has a section which is an abrasive surface.

9. The dental implant assembly as defined in claim 6 wherein said multiplicity of split segments are symmetrical segments.

10. The dental implant assembly as defined in claim 6 wherein said upper portion of said integral body member has a downward facing interior bore for adapting said top end of said internal shaft member.

11. The dental implant assembly as defined in claim 6 wherein said top end of said internal shaft member is integrally attached to said integral body member such that said internal shaft and said integral body member form a unitary piece.

12. The dental implant assembly as defined in claim 6 wherein said expander member has a frusto-conical shaped configuration.

13. The dental implant assembly as defined in claim 6 wherein said anti-rotation engagement means includes a multiplicity of downward protruding curved thin blades.

14. The dental implant assembly as defined in claim 6 wherein said means adaptable to a driving tool includes an upwardly extending polygonal lip.

15. The dental implant assembly as defined in claim 6 wherein said means adaptable to a driving tool includes a multiplicity of small dents.

16. A dental implant assembly for supporting a dental component on a patient's jawbone, the dental implant assembly to be fitted into a hole which is drilled in the jawbone and has an interior sidewall and a bottom, the dental implant assembly comprising:
   a. an implant member having a hollow bottom sleeve split into at least two segments, and a fixed shaft located inside the split bottom sleeve;
   b. an expander member movably mounted on said fixed shaft and having a ramped surface engaging with said at least two split segments; and
   c. said expander member engaged with said bottom of said jawbone hole, and caused to move on said shaft as said implant member is installed into said jawbone hole, to thereby force said at least two split segments of said bottom sleeve of said implant member to expand outwardly against and tightly engage with said interior sidewall of said jawbone hole;
   d. whereby said dental implant assembly can be securely installed into said patient's jawbone in a single step without any additional and separate step to operate said expander.

17. The dental implant assembly as defined in claim 16 wherein said implant member has means for adapting said dental component.

18. The dental implant assembly as defined in claim 16 wherein said at least two split segments are symmetrical segments.

19. The dental implant assembly as defined in claim 16 wherein said expander has means for anti-rotation engagement with said bottom end of said jawbone.

20. The dental implant assembly as defined in claim 16 wherein said implant member has means adaptable to a driving tool for rotating said implant member.

* * * * *